(12) United States Patent
Armau et al.

(10) Patent No.: US 6,620,609 B1
(45) Date of Patent: Sep. 16, 2003

(54) PROCESS OF MICROWAVE STERILIZATION OF CULTURE MEDIA FOR SELECTION OF RECOMBINANT MICROORGANISMS

(75) Inventors: Elise Armau, Toulouse (FR); Gérard Tiraby, Toulouse (FR)

(73) Assignee: Cayla, Toulouse (FR)

( * ) Notice: Subject to any disclaimer, the term of this patent is extended or adjusted under 35 U.S.C. 154(b) by 0 days.

(21) Appl. No.: 09/352,942

(22) Filed: Jul. 14, 1999

(30) Foreign Application Priority Data

Jul. 15, 1998 (EP) .............................. 98401784

(51) Int. Cl.$^7$ ........................... C12M 1/00; C12M 3/00; C12N 1/00; C12N 1/18; C12N 1/20
(52) U.S. Cl. ................. 435/253.6; 435/243; 435/252.1; 435/252.3; 435/252.33; 435/254.1; 435/254.2; 435/256.8; 435/260; 435/285.1; 435/404; 435/822
(58) Field of Search ................. 435/243, 822, 435/252.1, 252.3, 252.33, 253.6, 254.2, 800, 849, 252.8, 254.11, 256.8, 260, 285.1, 404

(56) References Cited

U.S. PATENT DOCUMENTS 5,500,367 A    3/1996   Hain et al. ............... 435/252.3
5,674,730 A   10/1997   Baim et al. ............... 435/240.2

OTHER PUBLICATIONS

Baqai et al.<< Microwave oven in microbiology laboratory >> The Journal of the Pakistan Medical Association, vol. 42 n° 1 Jan. 1992, pp. 2–3.

Keller et al. << Microwave treatment for sterilization of phytoplankton culture media >>. Journal of Experimental Marine Biology and Ecology 1988, vol. 117 n° 3 pp 279–283.

Tisserat et al. << Microwave sterilization of plant tissue culture media >> Publication HortScience, vol. 27(4) Apr. 1992 p 358–361.

WPIL Patent Abstract of FR 2 747 394.

Handbook of Microbiological Media, $2^{nd}$ Edition, by R.M. Atlas, pp. 743, 744, 1356, 1568 and 1573.

Primary Examiner—David M. Naff
Assistant Examiner—Deborah K. Ware
(74) Attorney, Agent, or Firm—Larson & Taylor PLC

(57) ABSTRACT

The invention relates to a process for a simplified and rapid preparation of sterile culture media using microwave ovens. The sterile media of the invention are usable for the selection and identification of microorganisms transformed by viral or plasmid DNA.

13 Claims, No Drawings

PROCESS OF MICROWAVE STERILIZATION OF CULTURE MEDIA FOR SELECTION OF RECOMBINANT MICROORGANISMS

FIELD OF THE INVENTION

Ongoing advances in nucleic acid (DNA and RNA) molecular biology have greatly contributed to the growth of knowledge in all fields of biology. The entire body of traditional disciplines in biology has benefited from this molecular biology contribution. Mention may be made of microbiology and its branches: bacteriology, mycology, parasitology and virology, but also of cellular biology, cellular physiology, molecular genetics, biochemistry, enzymology, immunology and animal physiology. Use of the potentials of nucleic acids has resulted in the appearance of new, hitherto unknown fields of investigation known by new terms such as genomics, molecular medicine, and gene therapy.

Recombinant DNA technologies have grown just as rapidly thanks to the use of the bacterium Escherichia coli. The K12 strain of Escherichia coli together with its many mutants has, over the years, become an essential intermediary in all operations involving nucleic acids. Any researcher using recombinant DNA in almost all fields of biology is led to work with this bacterium, particularly in the form known as transformed, as a result of the introduction of plasmid or viral DNA into the cell. This is how, for example, the great majority of recombinant DNA preparations, which may include fragments of natural or modified DNAs of different origins obtained from the realm of procaryotic and eucaryotic, archeons or even chemically synthesized, are made from vectors specific to Escherichia coli. Laboratory strains of the yeast Saccharomyces cerevisiae must also be mentioned as it is one of the most frequently used microorganisms for the production of recombinant DNA.

The transformation of a bacterium or of a eucaryotic microorganism by a vector is an operation that is frequently performed by researchers and is performed in two stages. The first stage consists in introducing the vector's DNA into cells by means of various techniques, and the second stage in selecting those cells in the population that have received and express the vector's genes. The proportion of cells that express the vector's genes among the total number of cells varies greatly according to the type of transforming DNA and the transfer procedure used. Even in the best cases the population of transformed cells is always small. Several methods have therefore been devised to select only those cells that express the new gene or genes introduced by the transforming DNA. All rely on the expression of a gene whose product gives a dominant character to the cell relative to non transformed cells. An example is the use of a gene that is resistant to an antibiotic that is normally toxic to the receiving microorganism. The addition of a given antibiotic to a microbial cell that has been in contact with the DNA carrying the gene that is resistant to the antibiotic either prevents growth or kills cells that do not express the transgene, according to the nature of the antibiotic, whereas on the contrary the transformed cells that have become resistant multiply to finally produce a pure culture of resistant cells. For practical reasons selection is usually done with solid media in a Petri dish. In this case each transformed cell produces an independent pure culture that appears as the formation of colonies on the surface of the medium contained in the Petri dish. The most frequently used antibiotics for selecting transformed clones in E. coli are ampicillin and carbenicillin among the penicillins, kanamycin and neomycin among the aminosides, tetracyclin, chloramphenicol and zeocin.

The use of selection markers is often associated with the use of identification markers, in other words genes that enable transformed colonies to be distinguished from colonies that do not express said transgene by a different color. The most popular system among researchers is that based on the expression of the lacZ gene of the Escherichia coli β-galactosidase. The action of this enzyme, either whole or reconstituted as in the alpha peptide system used in many of the cloning vectors in E. coli leads to hydrolysis of a colorless compound, 5bromo-4-chloro-3-indoxyl-β-D-galactopyranoside (or X-gal) to give a blue insoluble product. The presence of this coloring agent in solid media for E. coli, for example, leads to the appearance of blue colonies formed by cells producing an active β-galactosidase, whereas cells devoid of β-galactosidase produce white colonies. Many other chromogenic or fluorescent substrates of β-galactosidase are used for the same purpose of visual distinction of positive populations among a population of white or non fluorescent colonies. Similar chromogenic or fluorescent substrates are also often used to detect positive colonies for other enzymatic activities such as β-glucuronidase and alkaline phosphatase, for example.

Gene cloning in E. coli vectors no longer requires a level of qualification needing several years experience as was still the case in the 1980s. Acquisition of these standard technologies often begins at school and is carried on in molecular biology courses at university in any country with a strong scientific tradition. Methodologies relating to DNA and RNA manipulation have been greatly simplified by the introduction of successive improvements designed by the entire scientific community and propagated through publications. Another decisive element that has led to simplification and also to reduction of the time needed to perform experiments relating to DNA and RNA has come from companies specialized in the supply of products for research into and use of microbiology and molecular biology. By supplying equipment that is ready-to-use and contains all the elements needed to perform even the most complex experimental operations in biology these companies have greatly contributed to make these technologies more accessible. These companies readily impart information on any technological improvement discovered in the world's scientific and medical laboratories to their biologist clients. To date none of them offer the products and the methodology that are the subject of this invention.

The different stages in the transformation of a bacterium or of eucaryotic microorganisms such as yeasts and filamentous fungi by a DNA vector are broadly as follows: recipient cells enabled to incorporate DNA by means of various treatments are put into contact with the DNA and are then put into culture in a liquid medium to allow the appearance of the selection property before being spread in Petri dishes containing a solid medium with the addition of the selection agent. At this stage a chromogenic or fluorescent substrate may also be added for the cloning or transfer vectors as a means to identify the colonies. Following one night or several days incubation, according to the growth rate of the organism concerned, those cells that initially recovered the vector and express the transgenes form colonies. These colonies are then recovered in order to prepare cultures, this time in liquid media containing the selection agent, in order to extract the extrachromosomal DNA which is then characterized on the basis of size, the presence of restriction enzyme sites, and possibly by sequencing. The volume of liquid culture depends on the quantity of DNA sought by the researcher, and may vary from a few milliliters to one liter or more. These technologies, as applied for instance to microorganisms such as E. coli and S. cerevisiae, are well known to those familiar with the art, and their degree of difficulty in no way limits implementation of the invention.

BACKGROUND OF THE INVENTION

The invention relates to a new method of preparing selective liquid and solid media for the selection and manipulation of recombinant microorganisms. The selective media are at present prepared in an identical way by all experimental biologists all over the world. The ingredients that compose a given medium are mixed with water in variously shaped containers usually made of glass and closed either with a cork made of cotton, polyurethane foam, or any other matter permeable to air, able to withstand temperatures of 125–130° C. and wrapped in aluminum foil or closed with a screw cap made of bakelite or other resistant material. The container is then placed in an autoclave for sterilization, generally for 20 minutes at 120° C. After autoclaving the container is cooled to a temperature of 40–50° C. and only then is the antibiotic in a sterile solution, as well possibly as a sterile solution of a chromogenic or fluorescent substrate and an inductive molecule of the expression of a transgene, added aseptically to the medium in the container. These various additives cannot be included in the medium before autoclaving owing to their sensitivity to the temperature reached in the autoclave, and are therefore only added in the form of a sterile solution by filtering through a membrane in the medium following autoclaving. In the case of a medium containing agar the dishes are immediately prepared by spreading the melted medium in sterile Petri dishes.

The three stages of the sterilization cycle in the autoclave, i.e. the rise in temperature, the duration of maintenance at the desired temperature, and the fall in temperature, takes at least one hour. Performance of the other tasks involved in the process, that is preparation of the medium before autoclaving, cooling of the medium following opening of the door of the autoclave, addition of the additives and preparation of the Petri dishes takes at least another hour, bringing the total time of the operation to about two hours. If the problem of availability of the autoclave is added, a bulky apparatus which may be the only one in a laboratory, and which may not always be available for use at the time a researcher needs it most, and the cause of omissions or errors arising in the additions of antibiotics and other molecules to the medium, a process is achieved which so far has been necessary but represents a serious limitation to greater efficiency in the researcher's working time. A first solution at this level is the centralization of preparation of the media by one or a group of persons who ensure the supply of the culture media to a whole group of users. This situation can of course only exist in large units. A second possibility is the purchase of liquid media ready for use and Petri dishes ready for use, a solution which would be perfect were it not for the cost, a limiting factor for the budgets of many laboratories and teams both in the public and private sectors.

The use of microwave ovens has become general practice for the heating of food kept either at room temperature or refrigerated or deep frozen. The advantages of microwave ovens over traditional methods of heating food lie in the speed and ease of implementation. The high demand in the market has led to microwave ovens being so commonplace as to be as common in kitchens as refrigerators. A great variety of ovens, differing in wave strength, internal volume and programming options is now available on the domestic appliances market. Microwave ovens have also in past years found a place in laboratories for specific applications in molecular biology. Characterization of the size of nucleic acids is done by measuring migration distances following electrophoresis in agarose gel. Agarose, which is the solidifying agent of the gel, is a purified form of the gelose used to solidify culture media. A now widely used technique consists in melting the agarose with the addition of the aqueous buffer in a microwave oven in order to be able to pour the liquid solution into the vat of the electrophoresis apparatus to form the gel. Sterility of the gel is entirely unnecessary in this application, and only speed has led to the generalization of this technique as opposed to that which relies on fusion of the agar in an autoclave.

It would be very advantageous to be able to substitute the use of an autoclave by that of a microwave oven for the preparation of liquid and solid culture media. However the essential condition here is that the media must be completely sterile, in other words devoid of microorganisms. It is because microwave ovens have always been considered unable to ensure sufficient sterility that they have not been recommended for the preparation of culture media for microorganisms. Confirmation of this assertion is to be found in the basic reference book of every microbiologist (Handbook of Microbiological Media, second edition, 1997, by Ronald M. Atlas, Edited by Laurence C. Parks, CRC Press), which provides references to thousands of media, including their compositions and methods of preparation, but does not once mention the use of microwave ovens instead of autoclaves.

The effect of microwaves applied for periods compatible with the desired use is not sufficiently microbiocidal to kill all microorganisms present in the solid ingredients of media. Ingredients of media consisting of organic matter of animal, plant or microbial origin and mineral matter contain at different levels a great diversity of microorganisms.

One of the methods that make it possible to obtain sterile media by microwaving is to sterilize the raw materials used in the composition of the media before exposure to microwaves. The powdered mixture of each of the constituents may be sterilized, for example, by gamma irradiation in equipment already in use in establishments equipped to sterilize food. Maintenance of sterility of irradiated powder before use is ensured by aseptic storage of the powder in sterile packets containing a unit quantity of powder sufficient to prepare a given quantity of medium. The manufacture of culture media that meet the required sterility criteria is thus achieved by using these packets in the following conditions: a sterile container closed by a non metallic screw cap in which the contents of a packet corresponding to a given medium have been poured and mixed with the required quantity of water is placed in a microwave oven. The container is subjected to the effects of microwaves for about three minutes at the oven's maximum power with two or three regularly spaced pauses during which the container is agitated by rotation in order to facilitate a uniform dissolution of the powders, and the melting of the agar in the case of solid media. Following a 5 to 10 minute cooling period the corresponding antibiotic and other additives are added to produce a liquid medium ready for use or a solid medium ready to be poured for the manufacture of Petri dishes.

An even greater simplification of the preparation process of media by the use of microwaves would be achieved if the selection and identification agents were already present in the contents of the packet. A number of these additives have proven sensitive to temperatures generated by the microwaves and can therefore not be included in the powders.

OBJECTS AND SUMMARY OF THE INVENTION

However in the course of the great many trials made to perfect this new process, the applicant company has found that the constituents of the composition of some media played a thermoprotective role on additives sensitive to heat such as antibiotics of the penicillin type, or to X-gal, for example. Substances known to be cryoprotective and for their effect in protection during lyophilisation such as saccharose, trehalose, amylopectins, various starches as well as mannitol and sorbitol have proven in different degrees to increase the resistance of molecules to inactivation by heat generated by microwaves in aqueous solutions. Thanks to the addition of one of these stabilizing substances, the choice and concentration of which must take into account an absence of effect on the growth of the microorganism being studied, the present invention makes it possible to include most of the selection and identification additives of the recombinant microorganisms in the packets, thus eliminating a post microwave stage.

MORE DETAILED DESCRIPTION OF THE INVENTION

This discovery has moreover provided a new process for obtaining sterility of media subjected to microwaves. Sterility is obtained by the addition of substances that are toxic to microorganisms other than that to be cultivated in the medium being prepared and of a thermoprotective substance to the non sterilized powdered mixtures of the ingredients of the medium. In the case of *E. coli*, a gram negative bacterium, the addition of antibiotics that are specifically active on gram positive bacteria and of antifungal substances ensures, together with the addition of an antibiotic for the selection of transformants, a perfect sterility following exposure to microwaves without it being necessary to resort to sterilization by the efficient but costly operation of gamma irradiation.

In the case of yeasts, the addition of a wide spectrum antibacterial antibiotic and of the antibiotic for the selection of transformants of the yeast, such as zeocin, ensures perfect sterility and normal growth of the colonies.

EXAMPLE 1

The following example illustrates a whole series of experiments the results of which end in the same observation, which is that the heat generated by microwaves on an aqueous medium is insufficient to ensure sterility of the media, enabling use in microbiology and molecular biology.

The powdered constituents of the classic LB medium for *E. coli* needed for the preparation of 200 ml of medium the composition of, which is listed on page 743 of the Handbook of Microbiological Media (yeast extract of Bio Springer yeast 1 g, Difco casein pancreatic hydrolysate 2 g, NaCl 1 g, Difco agar 3 g) are weighed accurately and mixed in two 500 ml glass flasks closed by a screw cap. The same quantity of powder of the preconstituted LB medium (7 g) marketed by BIO101 is added in two other flasks. Following the addition of 200 ml of distilled water two flasks are autoclaved together at 120° C. for 20 minutes while the other two flasks are separately put through a microwave oven adjusted to medium power once for 3 minutes, and then twice for 30 seconds, each time after having been agitated for a few seconds. Following thermal treatment, the media show the same limpid pale straw color. Ampicillin in sterile solution is then added to each flask at the final concentration of 50 μg/ml and nine dishes are then poured from each of the agar media. A culture of the *E. coli* DH5 strain is prepared from appropriate cells put into contact with DNA of the pBR322 plasmid in the liquid LB medium for 90 minutes. A fraction of the culture is spread on three dishes obtained from each of the media in a sterile laminar flow apparatus. The dishes are then incubated at 37° C. Three non-inoculated dishes are also incubated at 37° C. for 48 hours and the other three at 27° C. for 7 days. The results are presented in table 1.

TABLE 1

| | Autoclaved medium | | Microwaved medium | |
|---|---|---|---|---|
| | unseeded | +DH5 Number of colonies | unseeded | +DH5 Number of colonies |
| Reconstituted medium | 37° C. sterile | 200 (e) | 37° C. a | f |
| | 37° C. sterile | 177 (e) | 37° C. a | f |
| | 37° C. sterile | 209 (e) | 37° C. a | f |
| | 27° C. sterile | | 27° C. b | |
| | 27° C. sterile | | 27° C. b | |
| | 27° C. sterile | | 27° C. b | |
| Preconstituted medium | 37° C. sterile | | 37° C. c | |
| | 37° C. sterile | | 37° C. c | |
| | 37° C. sterile | | 37° C. c | |
| | 27° C. sterile | | 27° C. d | |
| | 27° C. sterile | | 27° C. d | |
| | 27° C. sterile | | 27° C. d | | a-Dishes contain an average of 30 colonies of various sizes (from the size of a pin head up to 3 mm) and various colors (translucent to yellowish brown) showing heterogeneity of contaminating microorganisms.
b-Dishes are entirely covered by the heterogeneous mycelium belonging to two fungi, one white and one green.
c-Dishes contain about ten colonies most of which are homogeneous, measure 2 mm and are amber colored.
d-Dishes contain about 20 large white colonies attributed to yeasts buried under a white mycelium that entirely covers the dish.
e-Dishes only contain colonies of *E. coli*
f-Dishes contain colonies of *E. coli* mixed with colonies of contaminating organisms.

The results of the operation described in this example were reproduced every time the experiment was performed. Moreover it was found that the number and type of microbial contaminant observed with the microwaved media varied greatly according to the batches of raw materials that went into the composition of the selection medium coming from a same supplier or from different suppliers.

EXAMPLE 2

This example shows that repeated heating treatment of a non sterile aqueous medium by microwaves may however lead to sterility of such media as opposed to a single treatment.

A first series A consisting of 18 500 ml flasks containing 4 g of reconstituted powdered mixture of non gelosed LB medium (yeast extract of Difco yeast 1 g, Bio-Merieux biotrypcase 2 g, Prolabo NaCL 1 g) and 200 ml of tap water is prepared. A second series B consisting of 18 flasks containing 7 g of reconstituted powdered mixture of gelosed LB medium (extract of Difco yeast 1 g, Bio-Merieux casein pancreatic hydrolysate 2 g, Prolabo NaCL 1 g, Biokar gelose 3 g) and 200 ml of tap water is prepared. Six flasks of series A and six flasks of series B are autoclaved at 120° C. for 20 minutes. Each of the remaining flasks of both series is microwaved in an oven adjusted to maximum power once for 2 minutes, and then twice for 30 seconds after having been agitated slowly for a few seconds. Half the flasks of each series treated by microwaves once are retreated a second time according to the same process as above following an interval of at least one hour between the two treatments in order to allow the non gelosed medium to cool completely and the gelosed media to set in the flask. The series A flasks that have been autoclaved and microwaved once or twice are incubated without agitation at 37° C. and 27° C. The dishes are poured from the gelosed media and incubated in vats at 37° C. for 3 days and at 27° for 7 days. The results are presented in table 2 and table 3.

TABLE 2

Liquid medium - Series A

| T° | Flasks | Autoclaved | Microwaved once | Microwaved twice |
|---|---|---|---|---|
| 37° C. | 1 | Sterile | a | Sterile |
|  | 2 | Sterile | a | Sterile |
|  | 3 | Sterile | a | Sterile |
| 27° C. | 4 | Sterile | b | Sterile |
|  | 5 | Sterile | b | Sterile |
|  | 6 | Sterile | b | Sterile | a-The medium in the flasks, which was limpid at the beginning of incubation, became clouded at about 40 h. Observation of the densely clouded medium on day 3 with a phase contrast microscope revealed the presence of a dense population of mobile bacteria.
b-The medium in the flasks began to cloud at the end of day 3. Observation of the medium on day 7 with a phase contrast microscope revealed the presence of a population of bacteria apparently identical to those observed in the flasks incubated at 37° C.

TABLE 3

Solid medium - Series B

| T° | Flasks | Autoclaved | Microwaved once | Microwaved twice |
|---|---|---|---|---|
| 37° C. | 1 | Sterile | c | Sterile |
|  | 2 | Sterile | c | Sterile |
|  | 3 | Sterile | c | Sterile |
| 27° C. | 4 | Sterile | d | e |
|  | 5 | Sterile | d | Sterile |
|  | 6 | Sterile | d | Sterile | c-Dishes are covered with 200 to 300 colonies of various sizes, colors and shapes.
d-Dishes contain colonies of an average size of 1 mm covered by a white woolly mycelium.
e-The only dish in this series showing contamination in the form of a white filament veined with pink that covered the entire gelosed surface.

EXAMPLE 3

The following example shows sterility of microwaved media is obtained when the powders that go into the composition of the culture medium to be reconstituted with water are themselves sterile.

A 6 kg sample of the mixture of powders that go into the composition of the culture medium Terrific Broth that was developed in order to obtain dense cultures of $E.$ $coli$ and is well known to molecular biologists, and the composition of which is described on page 1356 of the Handbook of Microbiologica Media, is prepared in one batch (extract of Bio Springer yeast 3024 g, Difco tryptone 1512 g, Prolabo KH2PO4 1184 g, Prolabo K2HPO4 277 g). A large proportion (5 kg is sterilized by gamma irradiation in an apparatus used to sterilize foodstuffs destined for human consumption (GAMMASTER, France). The entire irradiated sample is then spread manually according to the aseptic experimental conditions used by all microbiologists in a laminar flow apparatus, in sterile aluminum foil packets in quantities of 10 g per packet. The packets are then heat sealed by means of an appropriate apparatus and stored at room temperature in a cardboard box.

The contents of each packet containing powder subjected to gamma irradiation or the same mixture of non irradiated powder is poured into a 500 ml flask and mixed with 200 ml of distilled water. Each flask is then microwaved at medium power for 3 minutes and twice for 20 seconds. After cooling 75 ml of medium sampled in aseptic conditions from each flask are put into three sterile Erlenmeyer flasks closed by foam corks. The Erlenmeyer flasks are agitated on an agitating table in a room thermostatically kept at 37° C. for one week. The appearance of microbial contaminants is monitored every day by visual observation of the turbidity of the medium in each flask and microscope observation of samples made from each flask in which the contents have clouded. The results are presented in table 4.

TABLE 4

| Flask | Erlenmeyer flask | Irradiated powder | Non irradiated powder |
|---|---|---|---|
| 1 | 1 | sterile | b |
|  | 2 | sterile | b |
|  | 3 | sterile | b |
| 2 | 1 | sterile | b |
|  | 2 | sterile | b |
|  | 3 | sterile | b |
| 3 | 1 | a | b |
|  | 2 | sterile | b |
|  | 3 | sterile | b | a-The only Erlenmeyer flask in this series that was contaminated from day 3.
b-The medium in all Erlenmeyer flasks in this series became cloudy between the end of the first and the second day of incubation.

Identical tests for sterility following microwaving were repeated three times over a period of several weeks with powder from the remaining packets. Results tallied with those presented in table 4, the media prepared from sterilized powder remaining sterile throughout the whole period of incubation, whereas all the flasks containing the medium prepared from untreated powders rapidly developed bacterial contamination.

EXAMPLE 4

This example shows that sterility of specific media for the selection of transformed colonies of $E.$ $coli$ for resistance to ampicillin can also be obtained by the addition of powdered antibiotics to the mixture of ingredients before they are dissolved in water through the effect of microwaves.

A preparation is made of a 1050 g sample of the mixture of powdered constituents of that make up the gelosed LB medium the recipe of which is described on page 743 of the Handbook of Microbiological Media: yeast extract of Bio Springer yeast 150 g, Biokar case in pancreatic hydrolysate 300 g, Prolabo NaCl 150 g, Difco agar 450 g to which are added 150 g of Roquette Freres amylopectin. The sample is divided into four equal parts equal to 300 g called batch A, batch B, batch C and batch D. To batch B is added 750 mg of powdered Sigma ampicillin. To batch C is added 750 mg of powdered Sigma ampicillin and 75 mg of Leo fusidic acid. To batch D is added 750 mg of powdered Sigma ampicillin, 75 mg of Leo fusidic acid and 75 mg of Sigma nystatin. The thoroughly homogenized mixtures of powders of batches A, B, C and D are divided into of 8 g samples and put into aluminum foil packets 5 cm by 9.5 cm in size that are then heat sealed.

Two 500 ml flasks are prepared for each batch by pouring the contents of one packet that is then resuspended in 200 ml of tap water. One flask of each batch is autoclaved for 20 minutes at 120° C. after which 9 dishes are poured. The second flask of each batch is microwaved in a microwave oven at maximum power for two minutes, and twice more for thirty seconds, between which the flask is agitated slowly outside the oven for a few seconds in order to facilitate homogenization of the medium, and then Petri dishes are poured.

A diluted portion of a culture of the relevant MC1061 strain of E. coli put in contact with DNA of the pUC19 plasmid, and following growth in an LB medium during 60 minutes is spread on three dishes of each batch having been prepared by autoclaving and three dishes of each batch having been prepared by microwaving. The inoculated dishes are incubated at 37° C. for 8 hours while of the six remaining non-inoculated dishes for each flask 3 dishes are incubated at 37° C. for three days and 3 dishes are incubated at 27° C. for one week. The results of the state of the dishes following incubation are presented in tables 5 and 6.

TABLE 5

| | Autoclaved medium | | |
|---|---|---|---|
| | unseeded dishes | | MC1061 |
| Batches | 37° C. | 27° C. | (pUC19) |
| Batch A | Sterile | Sterile | Film of E. coli |
| Batch B | Sterile | Sterile | Film of E. coli |
| Batch C | Sterile | Sterile | Film of E. coli |
| Batch D | Sterile | Sterile | Film of E. coli |

The results in this table clearly show that passage through the autoclave has destroyed the activity of the antibiotics added in the various batches of the medium since a uniform film of non transformed cells of the MC1061 strain covers all the dishes.

TABLE 6

| | Microwaved medium | | |
|---|---|---|---|
| | unseeded dishes | | MC1061 |
| Batches | 37° C. | 27° C. | (pUC19) |
| Batch A | 30 to 50 colonies of various sizes | Mycelium | Film of E. coli |
| Batch B | 10 colonies of 1 mm 2 woolly colonies 5 mm in size | Mycelium | Colonies of E. coli + Colonies of contaminant organisms |

TABLE 6-continued

| | Microwaved medium | | |
|---|---|---|---|
| | unseeded dishes | | MC1061 |
| Batches | 37° C. | 27° C. | (pUC19) |
| Batch C | 3 to 5 woolly colonies 5 mm in size | Mycelium | 118-145-190 colonies of E. coli + 3 woolly colonies |
| Batch D | Sterile | Sterile | 125-150-160 colonies of E. coli |

The results in this table show that the medium in batch D containing ampicillin, an antibiotic for transformant selection, fusidic acid, and antibiotic that is active on gram positive bacteria, and nystatin, an antifungal substance that is active on yeasts and filamentous fungi, produces, after microwaving, solid, perfectly sterile media that are compatible with an optimum selection of colonies of transformed cells. The number of colonies that appeared in dishes of microwaved medium D is identical to that observed in dishes prepared by the conventional method of sterilization of the selective medium and addition of ampicillin following autoclaving, inoculated with the same number of cells of the MC1061 strain. Moreover the DNA of the plasmid pUC19 is recovered in all clones prepared from colonies taken from dishes of medium D.

EXAMPLE 5

This example illustrates the preparation method of a standard E. coli medium for the selection of colonies resistant to ampicillin and colored blue or white according to the presence or absence of β-galactosidase activity based on the use of pre-prepared powders to be suspended in water and dissolved by means of a microwave oven. The advantages of this method in terms of simplicity and of time are clearly shown by comparison with the traditional method.

A sample of about 52 kg of powder formed by the mixture of the following ingredients: yeast extract of Biokar having low carbohydrate content 6250 g, Biokar tryptone 12500 g, Roquette Freres amylopectin 2500 g, Compagnie des Salins NaCl 6250 g, Prolabo Na2HPO4 6250 g, Sobigel agar 18750 g, Sigma ampicillin 125 g, Leo fusidic acid 12.5 g, Sigma nystatin 12.5 g, Biosynth IPTC (isopropyl-β-D-Thiogalactopyranoside) 125 g, Biosynth X-gal 62.5 g, is divided between aluminum foil packets 5.5 cm×9.5 cm in size in an automatic conditioning assembly line (Lallemand). One half of the packets marked Fast-Blue Amp and the other half Fast X-Gal Amp are filled with 8 g of powder and sealed on the assembly line without manual handling. Fast-Blue and Fast X-Gal are two different names for the same product that have been registered as trade marks in France. The packets have all been used in the Cayla company microbiology services in gene therapy in order to make a large scale evaluation of their potential for the preparation of dishes of selective media for the isolation of E. coli clones transformed by various native plasmids or arising from ligation substances during gene cloning experiments.

A typical use of the products Fast-Blue Amp and Fast X-Gal is as follows:

The contents of a packet are poured into a glass or plastic container resistant to temperatures above 100° C. of any shape and of a capacity of about 500 ml, that is to say compatible with the inside dimensions of the microwave oven used, and mixed with 200 ml of water, the minimum required quality of which being that it should be potable. The suspension is heated by the action of microwaves, only taking care not to exceed boiling point which would cause spilling of the medium out of the container. This condition is easily achieved by subjecting the container to flows of short waves interrupted by brief periods of agitation of the container to facilitate homogeneous dissolution of the ingredients in the container, which is handled using protective gloves against heat. This microwaving operation properly speaking is achieved in less than 5 minutes. The dishes are then filled following a pause of 5 to 10 minutes to allow the contents of the container to cool to a temperature that is more comfortable to the hands of the user, even though gloves are worn. The total duration of the preparation of dishes by this technique from the beginning of the operation, when the packet is taken, to the production of 8 to 10 Petri dishes is not more than 25 minutes, compared with the 2 hours necessary for the usual method in which the medium is autoclaved. Moreover the number of stages at which the researcher must intervene is reduced compared with the traditional method, thus considerably reducing the possibilities of errors which are often observed in the course of the addition of the selection antibiotic and other substances following autoclaving. In-house use by Cayla of thousands of packets of Fast-Blue and Fast X-Gal has made it possible to demonstrate the quality of media prepared by this method for the selection of transformed strains of *E. coli*. Experiments in comparison of solid media prepared from Fast products and microwaves and the traditional method have all shown that the time needed, the appearance of the blue color of colonies, and the intensity of the color are comparable if not more favorable for the methodology that is the subject of this invention. Moreover the size and number of colonies that appeared in the dishes were identical in all respects in both methods. This new technology has been validated with all receptive strains of *E. coli* tested, and a very great variety of plasmid vectors allow the white and blue distinction of colonies.

EXAMPLE 6

This example shows that the preparation method using microwaves of selective culture media for transformed bacteria apply equally to the selection of recombined eucaryotic microorganisms.

A preparation is made of a sample of about 1 kg of YEPD medium the composition of which is described on page 1573 of the Handbook of Microbiological Media: extract of Bio Springer yeast 150 g, Biokar mycopeptone 300 g, Roquette dextrose 300 g, Sobigel gelose 225 g, to which is added Merck Na2HPO4 45 g, Sigma ampicillin 1.5 g, Invitrogen zeocin 0.75 g. 14 g of this mixture is put into a 500 ml Erlenmeyer flask with 200 ml of twice distilled water, then the flask is microwaved in an oven adjusted to medium power for 2 minutes, 1 minute, and 30 seconds, and agitated for 5 seconds per rotation outside the oven during the two intervals. The liquefied medium is then divided into Petri dishes in a proportion of 25 ml per dish.

A culture of a laboratory strain of the yeast *Saccharomyces cerevisiae* OL1 ("MAT a leu2-3 leu2-112" his3-11 his3-15 ura3-251 ura3-373) is activated by the lithium method that is well known by professionals, and following contact with DNA of the pUT332 plasmid (Cayla) for 30 minutes, is diluted to 1/10 in the liquid YEPD medium. The culture is incubated under agitation at 30° C. for 6 hours and after cooling in crushed ice for one hour, a fraction is spread on dishes of the microwaved selection medium and dishes prepared in the traditional autoclave method of medium YNB (Handbook of Microbiological Media page 1568) supplemented with glucose, leucine and histidine. Following 3 days incubation at 30° C. the number of colonies that appeared in the dishes is identical in both media, the size of the colonies on the rich microwaved medium being double that of colonies that appeared on the defined medium. Dishes inoculated with the control culture, not having been in contact with the transformant DNA, remained devoid of colonies, including both those with the rich microwaved medium and those with the autoclaved defined medium. Verification of the phenotype of colonies that appeared on the microwaved medium showed that it indeed corresponded with that expected for transformants of the pUT 332 plasmid, in other words zeo (resistance to zeocin) and ura (ability to grow in a medium devoid of uracil).

What is claimed is:

1. A process of using microwave sterilization for the preparation of a sterile culture medium for the selection of recombinant microorganisms using the action of microwaves, said process consisting of the steps of:
    a. adding a selection agent and/or identification agent, and further adding a heat protective agent, to a suitable culture medium containing suitable culturing ingredients, wherein said adding step is carried out prior to microwave sterilization;
    b. mixing all said culturing ingredients in said suitable culture medium with said selection and/or identification agent, and heat protective agent, said culturing ingredients and said selection and/or identification agent and heat protective agent being in powder form, so as to obtain a mixture in powder form;
    c. mixing said mixture in powder form with a sufficient quantity of water to obtain a suspension of said powder in water; and
    d. subjecting said suspension of powder dissolved in water to heat by the action of microwaves in order to sterilize said suspension without raising pressure above ambient pressure by not raising temperature of said suspension above its boiling temperature and allow said suspension to become homogeneous.

2. A process according to claim 1, wherein said water is sterile and the mixture in powder form is sterilized by gamma irradiation before mixing the powder with said sterile water.

3. A process according to claim 1, wherein the selection agent added in step a, comprises an antibiotic selected from the group consisting of penicillin, aminosides, tetracycline, chloramphenicol and zeocin.

4. A process according to claim 3, wherein the culture medium is designed for gram negative bacteria and at least one antibiotic added in step a is specific to gram positive bacteria.

5. A process according to claim 4, wherein the gram negative bacteria are from the species *Escherichia coli*.

6. A process according to claim 3, wherein the culture medium is designed for eukaryotic microorganisms and at least one antibiotic added in step a has a large spectrum antibacterial activity.

7. A process according to claim 6 wherein the eukaryotic microorganisms are yeasts.

8. A process according to claim 1, wherein the identification agent added in step a comprises a chromogenic or fluorescent molecule.

9. A process according to claim 1, wherein an induction agent is further added during step a.

10. A process according to claim 9, wherein the induction agent added in step a comprises isopropyl-β-D-Thiogalactopyranoside (IPTG).

11. A process according to claim 1, wherein a molecule having antifungal activity is further added during step a.

12. A process according to claim 1, wherein the heat protective agent is selected from the group consisting of saccharose, trehalose, amylopectins, starches, mannitol and sorbitol.

13. A process according to claim 1, wherein said heat by the action of microwaves is provided by a microwave oven.

* * * * *